United States Patent [19]

Ledis et al.

[11] 4,286,963

[45] Sep. 1, 1981

[54] DIFFERENTIAL LYMPHOID-MYELOID DETERMINATION OF LEUKOCYTES IN WHOLE BLOOD

[75] Inventors: Stephen L. Ledis, Hialeah; David L. Chastain, Jr., Ft. Lauderdale; Harold R. Crews, Miami, all of Fla.

[73] Assignee: Coulter Electronics, Inc., Ill.

[21] Appl. No.: 96,697

[22] Filed: Nov. 23, 1979

[51] Int. Cl.$^3$ ...................... G01N 33/48; G01N 33/72
[52] U.S. Cl. .................................... 23/230 B; 23/913; 252/408
[58] Field of Search ............... 252/408; 23/230 B, 913

[56] References Cited

U.S. PATENT DOCUMENTS

| | | | |
|---|---|---|---|
| 3,874,852 | 4/1975 | Hamill | 252/408 X |
| 3,962,125 | 6/1976 | Armstrong | 23/230 B X |
| 3,964,865 | 6/1976 | Das | 252/408 X |
| 4,102,810 | 7/1978 | Armstrong | 252/408 |
| 4,185,964 | 1/1980 | Lancaster | 23/230 B |

FOREIGN PATENT DOCUMENTS

50-53091   5/1975   Japan ..................................... 23/230 B

*Primary Examiner*—Arnold Turk
*Attorney, Agent, or Firm*—Meredith P. Sparks

[57] ABSTRACT

This invention relates to a lytic diluent and a method for rapid lysing of red blood cells in whole blood for a differential determination of lymphoid and myeloid populations of leukocytes, and measurement of hemoglobin, particularly for use in automatic particle counting systems.

The diluent is a mixture of at least one quaternary ammonium salt having surface active properties, and an additive in suitable proportions, buffered to an acid pH of 3.5 to 5.0. The additive includes 2-phenoxyethanol and other short chain alkanols substituted by one phenyl or phenoxy, as well as certain polyhydroxy compounds.

When the reagent is employed in lower concentrations, an alkaline reagent comprising a quaternary ammonium salt and an alkali metal cyanide, buffered to an alkaline pH, may be added to complete the chromagen formation.

17 Claims, No Drawings

DIFFERENTIAL LYMPHOID-MYELOID DETERMINATION OF LEUKOCYTES IN WHOLE BLOOD

BACKGROUND OF THE INVENTION

This invention relates to a lytic diluent and a method for rapid lysing of red blood cells in whole blood for a differential determination of lymphoid and myeloid populations of leukocytes, and measurement of hemoglobin, particularly in automatic particle counting systems.

Much effort has been devoted to the development of satisfactorily automated leukocyte differential systems, and several types of instruments are now being used to replace the slow, and error prone manual differential counts. However, a need exists for reagent systems which will be easily adaptable to automatic blood counting instruments. In particular, it is desirable to develop reagents and methods for use with the Coulter Counter ® Model S Plus automated blood counter, manufactured by Coulter Electronics, Inc. of Hialeah, Fla., which will enable the Coulter volume data accumulated on a Coulter Channelyzer ®, to discriminate two populations of leukocytes: (1) a lymphoid (lymphocytes) population, and, (2) a myeloid (neutrophils, monocytes, eosinophils, and basophils) population. This information, even though not a complete differential, gives valuable screening data. As a screening tool for spotting abnormal leukocyte situations, such as infection, leukemia, and possibly immature leukocytes, this lytic diluent provides valuable information not contained in ordinary blood counts. Abnormal situations flagged out by this method would require further study to obtain information of diagnostic significance. The two-population information can be used to monitor the process.

A report of previous work with saponin lysed blood showed that red blood cells could be lysed completely, leaving leukocytes in good condition for electronic counting when (1) the saponin concentration is carefully controlled, and (2) lysing is terminated by glutaraldehyde fixation or stabilization with albumin, cold temperature and dilution.

A method of obtaining leukocyte distributions, using about one-half the concentration of detergent as Lyse S ®, results in poorly separated populations [J. M. England, et. al, Lancet, Mar. 1, 1975 page 492; J. M. England et. al, Lancet, May 22, 1976; J. M. England, et. al, J. Clin. Path., 27, 623 (1974); P. A. Wycherly and M. J. O'Shea, J. Clin. Path., 31, 271 (1978).] Experiments showed that this Lyse S ® at half concentration was too powerful and that the larger myeloid population was rapidly shrinking in volume during the data accumulation stage, resulting in very severe overlapping of the two populations. The degree of overlap was very dependent on how rapidly the sample could be counted. The lymphoid-myeloid ratio was calculated using a complex curve-fitting routine.

D'Angelo et. al, J. Clin. Path., 38 No. 6, 658-662 studied the use of Cetrimide ® with and without citrate-saline solution as a practical diluent for electronic white cell counts, but without differentiation of lymphoid-myeloid populations.

In U.S. Pat. No. 3,874,852 (1975), Hamill to Coulter Diagnostics, Inc., a formula is included for a composition containing quaternary ammonium salt detergent and cyanide to be employed as a lysing and chromagen-forming reagent for obtaining a single volume leukocyte count and hemoglobin determination in the Coulter Counter ® Model S. This composition is used in alkaline solution since in acid solution potassium cyanide is converted into hydrogen cyanide gas which is evolved causing loss of the cyanide ion from the reagent, as a poisonous gas.

Further investigation was required to use quaternary ammonium salts as lysing agents for obtaining the two-population leukocyte count.

The Coulter Counter ® Model S Plus automated blood counter requires the lyse to be completed within a few seconds of contact with whole blood. The lyse must degrade and digest the red blood cell membrane to a point where the membrane debris will have a small enough volume to be cleanly separated from the leukocytes. For the Coulter Counter ® Model S Plus system the leukocyte volume distribution needs to be completely stable for at least one minute. It is very desirable, however, to have the leukocyte distribution stable for longer periods, for example, several minutes or up to one to two hours, so that the distribution is unchanged during counting, or so that manual dilutions can be examined with a semi-automated device. Also, with longer periods, finger stick blood could be lysed and held for subsequent analysis. The lytic diluent should give good results both on freshly drawn blood, and blood that has been stored for 24 hours or more.

To achieve a simple and accurate analysis of the percentage of lymphoid cells and myeloid cells in blood, the two populations of leukocytes should be cleanly separated such that the valley between the red cell debris and the lymphoid peak is very close to the baseline of the channel, and sufficiently broad to allow setting a fixed threshold channel from which the lymphoid cells can be counted. Likewise the valley between the lymphoid and myeloid peaks must allow for setting a fixed channel number dividing the populations on all blood samples without problems caused by overlap of the populations. Curve fitting programs, and variable valley settings which reduce the ease and accuracy of the results should be avoided.

In addition to allowing the identification of the leukocytes, the lytic diluent must permit formation of a chromagen which gives a satisfactory correlation with the concentration of hemoglobin in the whole blood sample.

SUMMARY OF THE INVENTION

A lytic diluent for the rapid lysing of red blood cells in whole blood in order to make a differential determination of the lymphoid and myeloid populations of leukocytes, and also measure hemoglobin comprises a mixture of an aqueous saline solution of at least one quaternary ammonium salt having attached to the nitrogen a long chain alkyl group conferring surface active properties, and at least one additive selected from the group consisting of (1) a short chain alkanol substituted by phenyl or phenoxy, and (2) a polyhydric alcohol compound in suitable proportions, the mixture buffered with citrate to an acid pH within the range of 3.5 and 5.0. The additive serves to improve the separation of the leukocyte peaks and to increase stability.

The lytic diluents of this invention are blood diluents, rather than concentrates to be added to diluted blood. It was found that when whole blood is diluted in a typical diluent, such as Isoton II ®, treatment with a concentrated lysing agent gave poorer results. Blood may be diluted first with 0.9% saline before dilution into the new lysing diluent without any deterioration in the results.

Two concentrations of the lytic diluent may be employed. A weaker concentration of the lytic diluent gives excellent separation of the peaks and excellent long term stability, but may need the subsequent addition of an alkaline buffered cyanide reagent to obtain cyanmethemoglobin. This system shall be called the two-reagent system.

A stronger concentration of the lytic diluent gives good separation of the peaks, short term stability and a chromagen which is well correlated to the hemoglobin concentration but is not a "cyanmethemoglobin", this method being called the one-reagent system.

Both concentrations can be adapted to manual operation or to the Coulter Counter® Model S Plus, and other automated equipment to make available for diagnosis a new parameter, the lymphoid-myeloid leukocyte differential.

DESCRIPTION OF THE PREFERRED EMBODIMENTS

A quaternary ammonium salt having surface active properties advantageously is employed as a stromatolysing agent, with high speed destruction of erythrocytes to a level avoiding interference with the two volume leukocyte determination, and with rapid conversion of hemoglobin to a chromagen, for use in the determination of leukocyte count and hemoglobin in the blood. The quaternary ammonium salt having surface active properties can be any of the class of quaternary ammonium compounds characterized by the formula

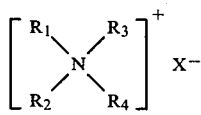

where one of the radicals $R_1$, $R_2$, $R_3$, $R_4$, is a long chain alkyl group conferring surface active properties, such as an alkyl radical having from 12 to 18 carbon atoms; and the remaining three radicals on the quaternary nitrogen are short chain alkyl groups having from 1 to 6 carbon atoms, or where any two of the three radicals, together with the nitrogen to which they are attached, form a heterocyclic ring such as pyridine or imidazole, and the third radical is short chain alkyl. $X^-$ is any salt forming radical, such as Cl, Br, I, $PO_4$, $HSO_4$, $CH_3SO_4$, or the like.

Preferred quaternary ammonium salts within the above description include quaternary ammonium halides having attached to the nitrogen three short chain alkyl groups and one long chain alkyl group, such as cetyl trimethyl ammonium chloride or bromide, myristyl trimethyl ammonium chloride or bromide, hexadecyl ethyl dimethyl ammonium bromide, and N-alkyl pyridinium halides such as N-cetyl pyridinium chloride or bromide.

The optimum concentration of quaternary ammonium salt required in the two-reagent system for the lytic diluent varies with the blood dilution to be used. For example, using a blood dilution of 1:220, the concentration of the lysing agent hexadecyltrimethyl ammonium bromide (Cetrimide®) is optimal at about 150 mg/l, depending in part on the quality of the Cetrimide® received from a supplier. When the blood dilution is changed to 1:400, the Cetrimide® concentration needs to be changed to 90 mg/l for satisfactory lysing. When a blood dilution of 1:400 is used, the leukocyte peaks are better resolved and more stable because coincidence of debris in the form of unlysed red blood cells in the counting aperture is reduced, but counting time should be increased to give satisfactory statistics.

When the above lytic diluent is used, a highly stable leukocyte distribution, with excellent separation of the peaks is obtained, but hemoglobin may not be completely converted to a chromagen characterized by a peak at 540 nm and valley of 505 nm (as is seen in cyanmethemoglobin). The solution of blood in the lytic diluent can be further treated, after the leukocytes are counted, with an alkaline buffered cyanide containing reagent to obtain a satisfactory hemoglobin derivative.

Alternately, a higher concentration of quaternary ammonium salt can be used which gives a good separation, and is stable for about one minute, but does not give long term stability. This one-reagent system gives a "cyanmethemoglobin"-like curve although it does not contain cyanide. The chromagen in this case is believed to be methemoglobin.

Lysing solutions prepared with distilled water in place of 0.9% NaCl are less effective for lysing red blood cells and preserving leukocytes.

The lysing agent, or combinations of lysing agents, are operable with the Coulter® Model S Plus, with modest changes in programming and mechanics of operation in addition to adding a Channelyzer® capability, and suitable method for calculating and printing out the results.

The two quaternary ammonium detergents, Mytab® (tetradecyltrimethylammonium bromide) and Cetrimide® (hexadecyltrimethylammonium bromide) were investigated to determine what concentration of either of these detergents give rapid, complete lysis of the red blood cells in whole blood, leaving a well separated and stable two-population leukocyte distribution.

Centrimide® at several concentrations and several pH values was tested on whole blood and the leukocyte distributions were studied as a function of time. The pH of the lysing solution was found to have a definite but modest effect on the ability of Cetrimide® to lyse red blood cells. The optimum concentration range for proper lysing is rather narrow, 80–200 mg/l Cetrimide®. One unexpected finding was that the pH of the lysing solution had a very dramatic effect on the stability of the two-volume leukocyte distribution. At a pH=about 4.0, this distribution is quite stable, but at higher pH such as 6.8, the myeloid peak rapidly degrades and merges with the lymphoid peak. Acid pH, particularly at pH=4.0, results in an initially cleaner and a far more stable two-volume distribution than more alkaline pH values. At pH lower substantially than 4.0 the results are not satisfactory.

A similar study was done using Mytab® as the detergent. Mytab® is a slightly less active lysing agent than Cetrimide® and a concentration of 300 mg/l Mytab® was needed for best leukocyte distribution. The effect of pH was the same with Mytab® as with Cetrimide®. Also, the distribution was not as stable using Mytab® instead of Cetrimide®.

Using 150 mg/l Cetrimide®, hundreds of blood samples were tested, both normal and abnormal, giving uniformly good red blood cell lysis except for samples containing nucleated red blood cells. Therefore, Cetrimide® has been used as the detergent of choice for the lysing agent.

Using a red blood cell calibrated Coulter Counter® Model H4 the volumes of the lymphoid and myeloid peaks were found to be in the vicinity of 145μ and 320μ respectively with narrow distribution widths. Leukocytes obtained from fresh whole blood by unit gravity sedimentation on Ficoll-Paque® had volumes of approximately 260μ for the lymphoid peak and 500μ for the myeloid peak with wide distribution widths. The separation of the populations was much better with the lysed blood than with the viable leukocytes obtained by the Ficoll-Paque® method. A sample of fresh blood was separated by centrifugation on Ficoll-Paque® to obtain the mononuclear cells (lymphocytes and monocytes) separated from the granulocytes (neutrophils, eosinophils and basophils) by a standard technique. The mononuclear cells, as expected, gave the lymphoid peak, 260μ (lymphocytes) and monocyte peak at 550μ which lies under the myeloid peak, with whole blood. The granulocytes form one myeloid peak at 500μ. It is apparent that the lysing agent damages the leukocytes since their volumes are substantially reduced compared to viable leukocytes obtained from the same blood sample; however, the lymphocytes show larger percentage of reduction in volume than the myeloids, resulting in a much better separation of the two white blood cell classes.

It has been found that in all lytic diluent formulations an additive is needed for good two-population distributions. Additives suitable for this purpose include a short chain alkanol substituted by one phenyl or phenoxy group, and certain polyhydroxy compounds. Examples of such alkanols include 2-phenoxyethanol, 1-phenyl-2-propanol, 3-phenoxy-1-propanol, 2-phenyl-1-propanol and 3-phenyl-1-propanol. 2-Phenoxyethanol is especially preferred for this purpose. Polyhydroxy compounds useful as additives include glycerol, propylene glycol, sorbitol, glucose and lactose. Mixtures of more than one additive will at times give improved results. The efficacy of the additive is also related to its concentration.

In order to demonstrate the effect of 2-phenoxyethanol in lytic diluent formulations of the two-reagent type, a formulation consisting of 150 mg/l Cetrimide®, and 0.2% citrate buffer to give a pH 4.0 in 0.9% NaCl, was treated with increasing concentrations of 2-phenoxyethanol. As little as 0.2% of 2-phenoxyethanol improved the separation of the myeloid and lymphoid peaks and also improved the separation of lymphoid from red blood cell debris. The separations improve and are maximized at 0.6–1.0% of 2-phenoxyethanol. When 2.0% of 2-phenoxyethanol is used, however, lysing is incomplete. At all of the concentrations tested the distribution was stable, being essentially unchanged after 2 minutes to 1 hour, depending on the formulation used.

The addition of 0.4–0.8% v/v of 1-phenyl-2-propanol, 3-phenoxy-1-propanol, 2-phenyl-1-propanol, or 3-phenyl-1-propanol to the lytic diluent results in excellent separation of the lymphoid from the myeloid peaks, but the debris level may be excessive in some blood samples and tend to merge into the lymphoid peak. 2-Phenoxyethanol is the best single additive for separation of debris, lymphoid and myeloid peaks, and stability. Mixtures of 2-phenoxyethanol and the above mentioned alcohols also give acceptable results as additives.

The stability resulting by addition of 2-phenoxyethanol to a lytic diluent formulation of the one-reagent type was different. Without 2-phenoxyethanol, the formulation of 250 mg/l Cetrimide®, 200 mg/l Mytab®, and 0.2% citrate buffer to give a pH 4.0 in 0.9% NaCl gave a moderately good distribution which was stable for one minute. Addition of up to 0.6% of 2-phenoxyethanol improved the separation of the leukocyte peaks, but tended to destabilize the distribution. The results at one minute, however, which is sufficient time for a leukocyte count when using the Coulter® Model S Plus, was good.

Using polyhydroxy compounds, the addition of 5% to 10% glycerol to the one-reagent lytic diluent improves the separation of the lymphoid and myeloid peaks and reduces the red blood cell debris, as compared with formulations prepared from distilled water or 0.9% saline. Other polyhydroxy compounds tested as additives include propylene glycol, glucose, lactose, sorbitol, and sucrose. These additives, in the range of 2 to 8%, had a substantial effect on the leukocyte histogram.

Using mixtures of more than one additive, adding 5% glucose to a formulation having 250 mg/l Cetrimide®, 200 mg/l Mytab®, 0.2% citrate, and 0.6% 2-phenoxyethanol at a pH 4.0, gives an improved separation and slightly better stability. Addition to 5% sorbitol gives a superior separation at one minute, and slightly better stability.

PREFERRED FORMULATIONS

One Reagent System—Stronger Concentration of Lysing Agent 250 mg/l Cetrimide® (hexadecyltrimethyl ammonium bromide)
200 mg/l Mytab® (tetradecyltrimethyl ammonium bromide)
0.6% (v/v) 2-phenoxyethanol
0.2% (w/v) citric acid; adjust final solution to pH 4.0 with 4 N sodium hydroxide
Optional additive—5% (w/v) sorbitol Solution is prepared in 0.9% (w/v) sodium chloride.

Although Mytab® is a poorer red blood cell lysing agent than Cetrimide®, it is considerably more active for hemoglobin conversion. A mixed lysing reagent containing 250 mg/l Cetrimide® for efficient red blood cell lysing plus 200 mg/l Mytab® for hemoglobin conversion is, therefore, preferred.

The addition of 0.6% of 2-phenoxyethanol not only improves the leukocyte distribution, but also improves the hemoglobin chromagen curve. The peak absorbance is at 530 nm, the minimum is at 500 nm, and a weak shoulder is present at 640 nm. The overall absorbance is markedly higher. This chromagen is formed in the absence of cyanide ion, and is not "cyanmethemoglobin" but the peak absorbance correlates well to the hemoglobin concentration.

The presence of 5% sorbitol improves the separation of the peaks, but retards the formation of methemoglobin.

The chromagen formation with the stronger concentration of lysing agent is comparatively slow, requiring 30–60 seconds to go to completion depending on additives used.

Two Reagent System—Weaker Concentration of Lysing Agent (a) Lysing Reagent 150 mg/l Cetrimide ® (hexadecyltrimethyl ammonium bromide)
0.8% (v/v) 2-phenoxyethanol
0.2% (w/v) citric acid (adjust final solution to pH 4.0 with 4 N sodium hydroxide)
Solution is prepared in 0.9% sodium chloride.

(b) Alkaline Cyanide Reagent 35 g/l Mytab ® (tetradecyltrimethyl ammonium bromide)
350 mg/l potassium cyanide
100 g/l $Na_2HPO_4.7H_2O$ Yellow dye or other identifying agent can be added, if desired.

The above formulation provides excellent two-volume leukocyte distributions with long-term stability. Such a solution is useful when data collection will be delayed as, for example, when finger-stick blood is collected in the weaker concentration of lysing agent; when blood dilutions are made manually for use on a semi-automatic counter; and when data collection is slow.

The lysing agent (a) does not convert completely the hemoglobin to a chromagen similar to the Lyse S ® chromagen, but requires that an additional reagent be added after the white blood cell count to complete the conversion.

Since this lysing agent is acid, cyanide cannot be incorporated in it; neither can cyanide alone be added to it. A cyanide reagent (b) which is similar to Lyse S ®, but which contains an alkaline buffer, was formulated for use on the Coulter Counter ® Model S Plus, and is effective when 0.78 ml of reagent (b) is added to 10 ml of reagent (a) containing the blood sample. The alkaline buffer is sufficient to bring the mixture of about pH 7, so that escape of hydrogen cyanide will not be a problem.

Addition of the alkaline Cyanide Reagent (b) to blood in lysing reagent (b) gives a very rapid (less than 5 sec.) conversion of the hemoglobin to a chromagen which appears to be identical to the Lyse S ® chromagen.

The use of this two reagent system works very well manually, and has been adapted for use on the Coulter Counter ® Model S Plus.

Over one hundred specimens obtained from a blood donor center and a large number of abnormal blood specimens obtained from a hospital were run on the Coulter Counter ® Model S Plus, adapted to operate with formulations containing stronger concentrations of the lysing agents. The leukocyte data was collected, and percentages of the lymphoid and myeloid cells were calculated. These results were compared with the manual 100 cell differential counts made from smears of the blood samples. In a large majority of the samples, the differentials agreed with the lymphoid-myeloid percentages obtained on the Coulter Counter ® Model S Plus. A group of normal samples were compared, using a 500 cell differential count performed in-house. These were all in very close agreement with the Coulter Counter ® Model S Plus data.

On a series of 28 blood samples, the hemoglobin concentration was obtained using the Lyse S ® method now being run on the Coulter Counter ® Model S Plus. The same blood samples were run using the stronger concentration of the lysing agent (One Reagent System) to obtain the hemoglobin concentration. These blood samples were also subjected to a manual cyanmethemoglobin determination. The correlation coefficient of Lyse S ® and new lysing agent to manual samples was satisfactory. The closeness of correlation of the hemoglobin concentrations was found to depend primarily on the quality of the manual hemoglobin data.

A similar study of normal bloods and abnormal clinical bloods was done using the weaker concentrations of Lysing agent plus alkaline cyanide reagent (Two Reagent System) on a Coulter Counter ® Model S Plus which had been modified for this purpose. The lymphoid-myeloid ratio and the hemoglobin concentrations were in excellent agreement with manual methods.

We claim:

1. A lytic diluent comprising a mixture of ingredients (A) and (B) where
    (A) is an aqueous saline solution of at least one quaternary ammonium salt having surface active properties, and
    (B) is at least one additive selected from the group consisting of
        (1) a short chain alkanol substituted by phenyl or phenoxy; and
        (2) a polyhydroxy compound;
said lytic diluent being buffered to an acid pH within the range of 3.5 to 5.0, and each of said ingredients (A) and (B) being present in an amount sufficient to bring about rapid and complete lysing of the red cells in whole blood for making a differential determination of lymphoid and myeloid populations of leukocytes, and also for measuring hemoglobin by chromagen formation.

2. The lytic diluent of claim 1 wherein said quaternary ammonium salt is selected from the group of compounds having the formula

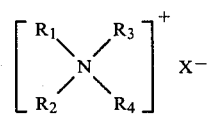

where one of the radicals $R_1$, $R_2$, $R_3$ and $R_4$ is a long chain alkyl radical having from 12 to 18 carbon atoms, and the remaining radicals are short chain alkyl radicals having from 1 to 6 carbon atoms, and compounds where two of the radicals together with the nitrogen to which they are attached form a heterocyclic ring; and $X^-$ is Cl, Br, I, $PO_4$, $HSO_4$, $CH_3SO_4$.

3. The lytic diluent of claim 1 wherein said quaternary salt is tetradecyltrimethyl ammonium bromide.

4. The lytic dilutent of claim 1 wherein said quaternary salt is hexadecyltrimethyl ammonium bromide.

5. The lytic diluent of claim 1 wherein said quaternary ammonium salt is a mixture of hexadecyltrimethyl ammonium bromide and tetradecyltrimethyl ammonium bromide.

6. The lytic diluent of claim 1 wherein said additive is sorbitol.

7. The lytic diluent of claim 1 wherein said additive is 2-phenoxyethanol.

8. The lytic diluent of claim 7 wherein said 2-phenoxyethanol is present in a concentration of about 0.2% to 1.0%.

9. The lytic diluent of claim 1 wherein said quaternary ammonium salt is present in a concentration in the range of about 200 to 500 mg/liter by weight of said solution.

10. A lytic diluent comprising a mixture of ingredients (A) and (B) where
  (A) is an aqueous saline solution of at least one quaternary ammonium salt having surface active properties, and
  (B) is at least one additive selected from the group consisting of
    (1) a short chain alkanol substituted by phenyl or phenoxy; and
    (2) a polyhydroxy compound;
said lytic diluent being buffered to an acid pH within the range of 3.5 to 5.0, and each of said ingredients (A) and (B) being present in an amount sufficient to bring about rapid, but incomplete, lysing of the red cells in whole blood for making a differential determination of lymphoid and myeloid populations of leukocytes, and also for measuring hemoglobin for chromagen formation, wherein said chromagen formation is completed by the addition of an alkaline reagent comprising an aqueous solution of a quaternary ammonium salt and an alkali metal cyanide, the mixture being buffered with a basic buffer in sufficient concentration to allow rapid neutralization of said lytic diluent which is buffered to an acid pH.

11. The lytic dilutent of claim 10 wherein said quaternary ammonium salt is present in a concentration of about 80 to 200 mg/liter by weight of said solution, and said chromagen formation is completed by subsequent addition of an alkaline reagent comprising an aqueous solution of said quaternary ammonium salt and alkali metal cyanide, buffered with a basic buffer in sufficient concentration to allow rapid neutralization of said acid lytic diluent.

12. The lytic diluent of claim 10 wherein said alkali metal cyanide is present in a concentration in the range of 200 to 400 mg/liter.

13. The lytic diluent of claim 10 wherein said basic buffer is selected from the group consisting of disodium hydrogen phosphate and dipotassium hydrogen phosphate.

14. A method for the differential determination of lymphoid and myeloid populations of leukocytes and also for measuring hemoglobin by chromagen formation which comprises employing a diluent which is a mixture of ingredients (A) and (B) where
  (A) is an aqueous saline solution of at least one quaternary ammonium salt having surface active properties, and
  (B) is at least one additive selected from the group consisting of
    (1) a short chain alkanol substituted by phenyl or phenoxy; and
    (2) a polyhydroxy compound;
said lytic diluent being buffered to an acid pH within the range of 3.5 to 5.0; and each of said ingredients (A) and (B) being present in an amount sufficient to bring about rapid and complete lysing of red cells in whole blood for making a differential determination of lymphoid and myeloid populations of leukocytes, and also for measuring hemoglobin by chromagen formation.

15. The method of claim 14 wherein said quaternary ammonium salt is a mixture of hexadecyltrimethyl ammonium bromide and tetradecyltrimethyl ammonium bromide, which is present in the range of about 200 mg to 500 mg/liter by weight of said solution.

16. A method for the differential determination of lymphoid and myeloid populations of leukocytes and also for measuring hemoglobin by chromagen formation which comprises employing a diluent which is a mixture of ingredients (A) and (B) where
  (A) is an aqueous saline solution of at least one quaternary ammonium salt having surface active properties, and
  (B) is at least one additive selected from the group consisting of
    (1) a short chain alkanol substituted by phenyl or phenoxy; and
    (2) a polyhydroxy compound;
said lytic diluent being buffered to an acid pH within the range of 3.5 to 5.0, and each of said ingredients (A) and (B) being present in an amount sufficient to bring about rapid, but incomplete, lysing of red cells in whole blood for making a differential determination of lymphoid and myeloid populations of leukocytes, and also for measuring hemoglobin by chromagen formation, wherein said chromagen formation is completed by the addition of an alkaline reagent comprising an aqueous solution of a quaternary ammonium salt and an alkali metal cyanide, the mixture being buffered with a basic buffer in sufficient concentration to allow rapid neutralization of said lytic diluent which is buffered to an acid pH.

17. The method of claim 16 wherein said quaternary ammonium salt in said diluent is hexadecyltrimethyl ammonium bromide which is present in a concentration of about 80 to 200 mg/liter of said solution, and said chromagen formation is completed using as quaternary ammonium salt tetradecyltrimethyl ammonium bromide in a concentration of about 30 to 50 mg/liter.

* * * * *